United States Patent
Wong et al.

[11] Patent Number: 5,547,364
[45] Date of Patent: Aug. 20, 1996

[54] TIPPING DEVICE AND METHOD OF PRODUCING MEDICAL CATHETERS

[75] Inventors: Chang-Ming Wong; Shihn-Juh Liour, both of Hsin Chu, Taiwan

[73] Assignee: Industrial Technology Research Institute, Hsin Chu Hsien, Taiwan

[21] Appl. No.: 325,602

[22] Filed: Oct. 19, 1994

[51] Int. Cl.⁶ .................................................. B29C 55/22
[52] U.S. Cl. ........................... 425/384; 264/291; 425/392; 425/393
[58] Field of Search .................. 425/302.1, 384, 425/392, 393; 264/291

[56] References Cited

U.S. PATENT DOCUMENTS

| | | | |
|---|---|---|---|
| 4,212,204 | 7/1980 | St. Amand | 264/291 |
| 4,404,159 | 9/1983 | McFarlane | 264/296 |
| 4,661,300 | 4/1987 | Daugherty | 264/40.6 |
| 4,834,637 | 5/1989 | Conta et al. | 425/173 |
| 4,904,433 | 2/1990 | Williamitis | 264/130 |
| 5,102,324 | 4/1992 | Bullard et al. | 425/135 |
| 5,209,882 | 5/1993 | Hattori et al. | 264/291 |

*Primary Examiner*—James P. Mackey
*Attorney, Agent, or Firm*—Jacobson, Price, Holman & Stern, PLLC

[57] ABSTRACT

A tipping device and processing for medical catheters, the device including a pneumatic mechanism, two fixtures controlled by the pneumatic mechanism to hold two opposite ends of the catheter, a nozzle controlled to heat or cool down the catheter, and hydraulic cylinder controlled to pull the catheter during the heating. When the front part of the catheter is heated and pulled, the outer diameter of the front part of the catheter is gradually reduced toward the middle, then the catheter is cooled down and removed from the device and then cut into a tapered tip.

6 Claims, 5 Drawing Sheets

INSERTING THE STEEL NEEDLE INTO
THE CATHETER

HOLDING DOWN THE CATHETER WITH
THE NEEDLE BY THE CLAMPING
DEVICE

SETTING : 1. THE HEATING TIME AND
            HEATING TEMPERATURE
         2. THE MOVING SPEED AND
            DISTANCE OF THE
            HYDRAULIC CYLINDER

HEATING THE CATHETER

STRETCHING THE CATHETER

STOPPING THE STRETCH AND COOLING
DOWN THE CATHETER

RELEASING THE CLAMPING DEVICE
AND REMOVING THE CATHETER

CUTTING THE FRONT END OF THE
CATHETER INTO A TAPERED TIP

RETURNING TO THE STAND-BY POSITION

FIG 6

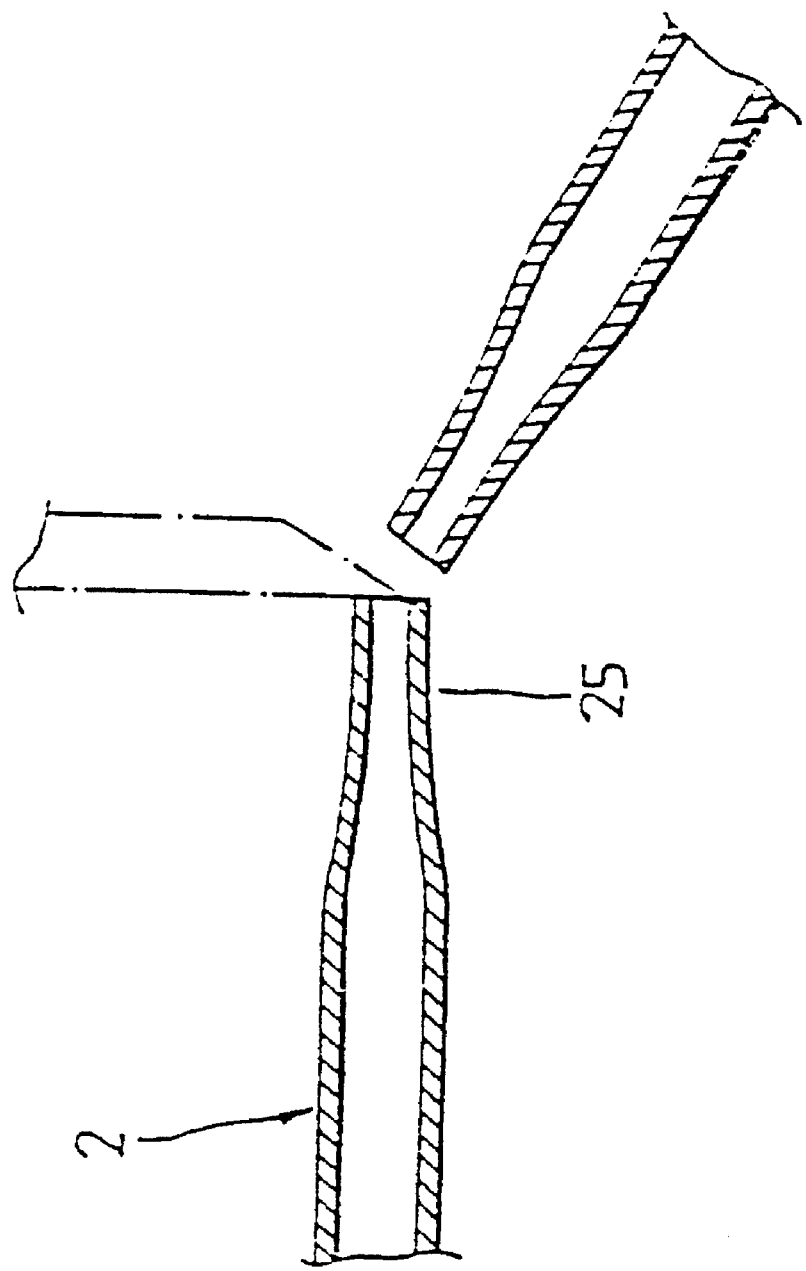

5,547,364

TIPPING DEVICE AND METHOD OF PRODUCING MEDICAL CATHETERS

BACKGROUND OF THE INVENTION

Thermoplastic polyurethane (TPU) has been extensively used for producing a variety of medical catheters. Medical catheters, including central venous catheters (CVC), bilumen catheters, trilumer catheters, etc., are commonly used for delivering medicine into the body, or else for drawing blood samples. The inserting end of a medical catheter must be tipped so that it can be conveniently inserted into the body without rendering serious damage to the tissues. Tipping the inserting end is relatively difficult since the outer diameter of regular medical catheters is commonly smaller than 3 mm and its wall thickness is smaller than 0.5 mm. Therefore, proper equipment and a good manufacturing process must be employed for producing medical catheters.

U.S. Pat. No. 4,264,294 of 1981 discloses a conical mold and its processing for the production of medical catheters. U.S. Pat. No. 4,404,159 of 1983 discloses an equipment and process for tipping medical catheters, which is comprised of a movable mold and base for holding the catheter. Wherein, the mold includes a bottom die coupled to an electric heater and a top die coupled to a cooling system. Furthermore the base is comprised of a piston supported on a spring, and a steel needle coupled to the piston. During the tipping process, a catheter is inserted with a steel needle and mounted on the base. Next, the mold is moved to the catheter, thereby permitting the front end of the catheter to be received in the tapered cavity of the mold. The electric heater is turned on to heat the bottom die in order to cause the front end of the catheter to be molded into a tapered tip. Finally, the catheter is removed from the mold and the steel needle after cooling.

U.S. Pat. No. 4,661,300 of 1987 discloses an apparatus and method for tipping medical catheters. The apparatus includes a radio-frequency generator to heat a mold, coolant to cool down the mold and a heated catheter, an infrared sensor to detect the temperature of the mold. During the tipping process, a catheter with a steel needle is mounted on a carriage and moved into the mold by a driving mechanism. The mold is heated by a radio-frequency generator and the front end of the catheter molded into a tapered tip. Next, coolant is applied to the mold to cool down the mold and the catheter. When the temperature of the mold reaches a predetermined value, the catheter is removed from the mold.

U.S. Pat. No. 4,904,433 of 1990 discloses the application of a lubricant to the surface of the catheter so that the catheter can be easily removed from the mold after molding. U.S. Pat. No. 5,102,324 of 1992 discloses the application of AC motor and a belt transmission in a tipping apparatus to move the catheter into the mold.

The aforementioned apparatus and processes are commonly to either move the catheter into the mold for heating and molding or to move the top and bottom dies to the catheter to heat and mold the front end of the catheter into a tapered tip. When the catheter is inserted into the mold during the tipping process, any small error may cause the surface of the catheter to become wrinkled or deformed, and melted material may be left in the mold. Furthermore, the mold needs to be heated first and then cooled down when molding, thereby subsequently resulting in a relatively long production cycle.

SUMMARY OF THE INVENTION

The present invention has been accomplished to provide a tipping device and method of producing medical catheters which eliminates the aforesaid drawbacks.

The present invention uses a heat source to heat the catheter at a suitable location, then stretch the heated catheter in the reversed directions. Consequently, the heated part of the catheter is gradually reduced in diameter. When the deformed part of the catheter is cut, the front end of the catheter forms into a tapered tip.

The method of the present invention is comprised of the steps of (1) inserting a steel needle into the catheter then mounting the catheter on the projecting pin of a movable board then manipulating the fixtures to hold down the catheter; (2) heating the catheter; (3) moving the movable board, which causes the catheter to become stretched in the reversed directions; (4) cooling down the catheter; (5) releasing the catheter from the fixtures; (6) removing the catheter from the tipping device and the steel needle; (7) and cutting the deformed portion of the catheter so as to obtain a tapered tip on the catheter.

BRIEF DESCRIPTION OF THE DRAWINGS

FIG. 6 is a block diagram showing the processing flow of the present invention; and FIG. 7 is a sectional view showing the processed catheter cut.

DETAILED DESCRIPTION OF THE PREFERRED EMBODIMENT

Figure 1:
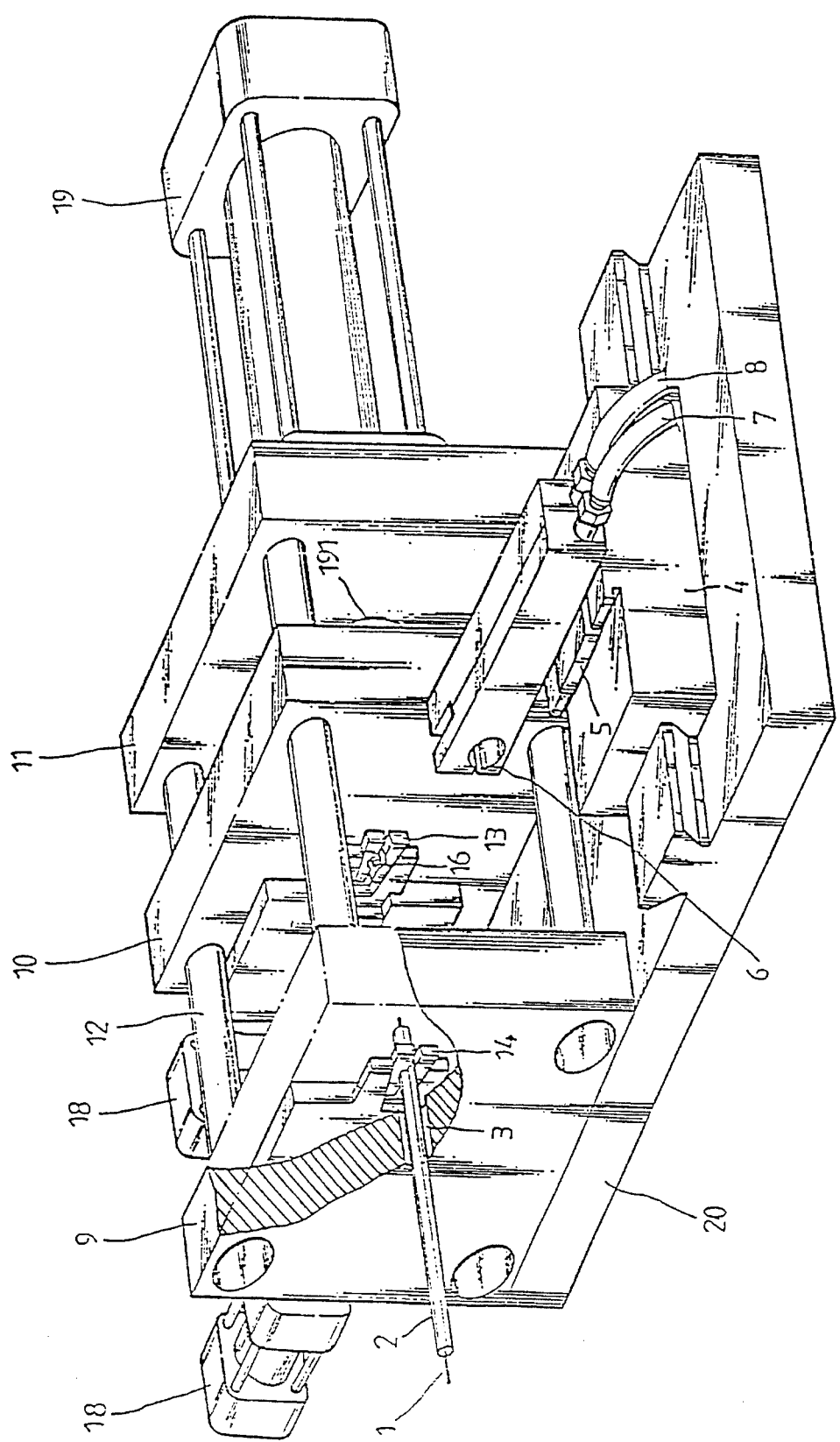
FIG. 1 is an elevational view of a tipping device according to the present invention.

Referring to FIG. 1, a tipping device according to the present invention is generally comprised of two fixed boards 9 and 11, a movable board 10, a hydraulic device 19, two fixtures 13 and 14, a steel needle 1, an air pump 18, and a nozzle 6. The fixed boards, i.e., the first fixed board 9 and the second fixed board 11, are vertically fixedly mounted on the base 20 of the tipping device at the top and disposed in parallel. Four circular tie rods 12 are connected in parallel between the fixed boards 9 and 11 in four corners. The movable board 10 is mounted on the tie rods 12 and moved in parallel between the fixed boards 9 and 11. The hydraulic device 19 is mounted on the second fixed board 11, having a piston rod 191 inserted through a hole (not shown) on the second fixed board 11 and coupled to the movable board 10. The piston rod 191 is controlled by a control device (not shown) to move the movable board 10 along the tie rods 12. Fixtures 13 and 14 are mounted on the first fixed board 9 and the movable board 10, respectively.

Referring to FIG. 1 again, the structure and installation position of the fixture 13 on the movable board 10 is similar to the fixture 14 on the first fixed board 9. The first fixed board 9 has a hole 3 aimed at the clamping center of the fixture 14. The diameter of the hole 3 is slightly larger than the outer diameter of the catheter 2 to be tipped such that the catheter 2 can be inserted into the hole 3 and clamped into position by the fixture 14. The movable board 10 has a circular pin 16 raised from the first side and is longitudinally aligned with the hole 3. The outer diameter of the circular pin 16 is slightly smaller than the inner diameter of the catheter 2 such that the front end of the catheter 2 can be mounted on the circular pin 16 and clamped into position by the fixture 13.

Before the processing, the steel needle 1 is inserted into the catheter 2. Next, the catheter 2 with the steel needle 1 are inserted through the hole 3, thereby permitting the front end of the catheter 2 to be mounted on the circular pin 16. The air pump 18 is then operated to move the fixtures 13 and 14, subsequently causing the fixture 14 on the first fixed board 9 to clamp the catheter 2 and the steel needle 1 and the fixture 13 on the movable board 10 to clamp the catheter 2 and the circular pin 16.

The nozzle 6 is disposed adjacent to the imaginary line passing through the hole 3 and the circular pin 16 and is controlled to heat or cool down the catheter 2. A heating device (not shown) is controlled to produce a current of hot air permitting it to be sent out of the nozzle 6 through a hot air pipe 7 to heat the catheter 2. For cooling the catheter 2, cooling air is sent out of the nozzle 6 through a cold air pipe 8. The nozzle 6 is supported on two slide carriages 4 and 5. The slide carriage 4 is moved in the direction parallel to the circular tie rod 12. The slide carriage 5 is moved in the direction perpendicular to the circular tie rod 12.

Figure 2:
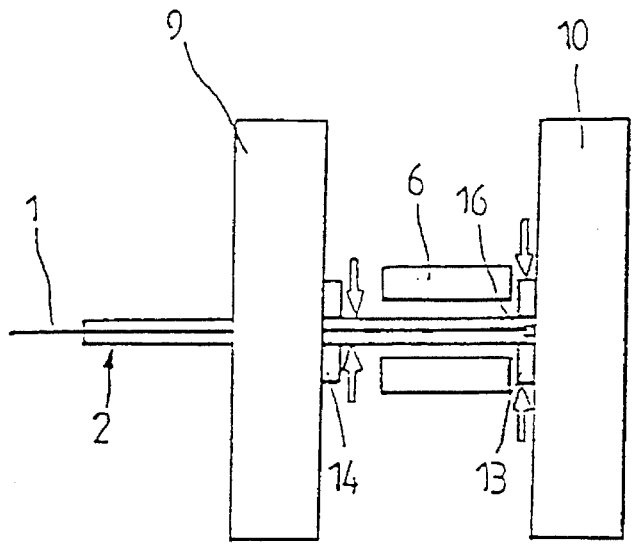
FIG. 2 is an applied view of the present invention showing the catheter mounted on the tipping device and clamped in position by the fixtures.
Figure 3:
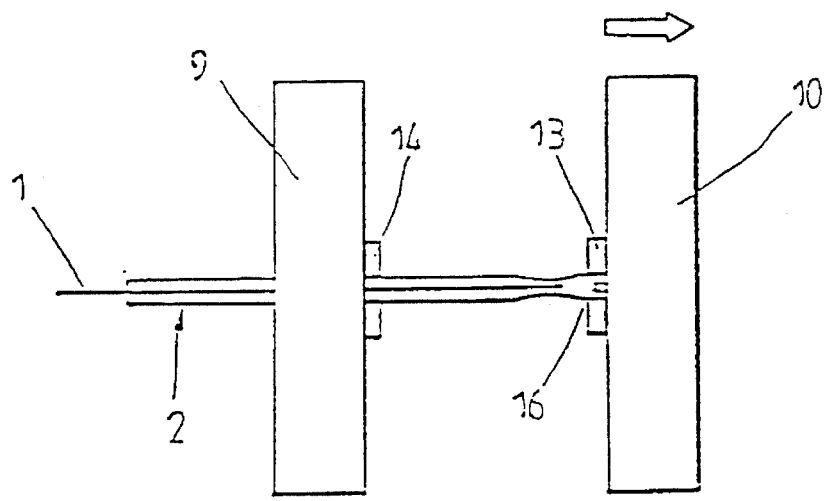
FIG. 3 shows the catheter of FIG. 2 heated and stretched in the reversed direction.
Figure 4:
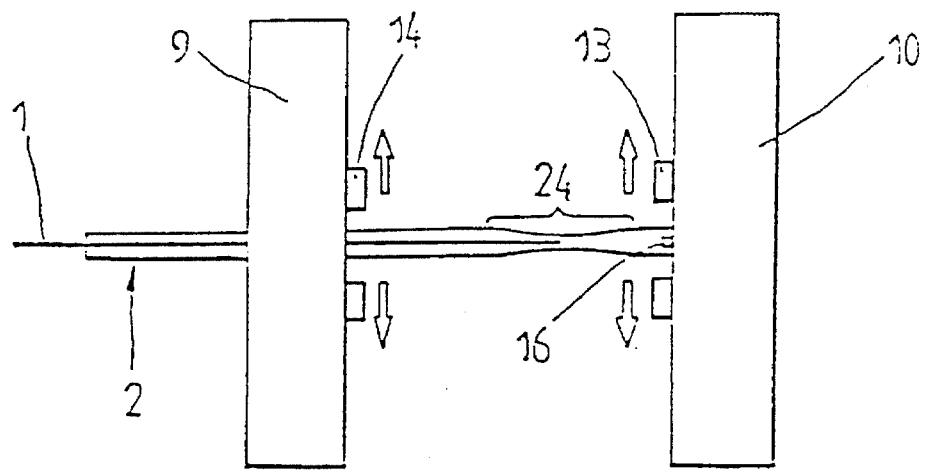
FIG. 4 shows the catheter of FIG. 3 released from the fixtures.
Figure 5:
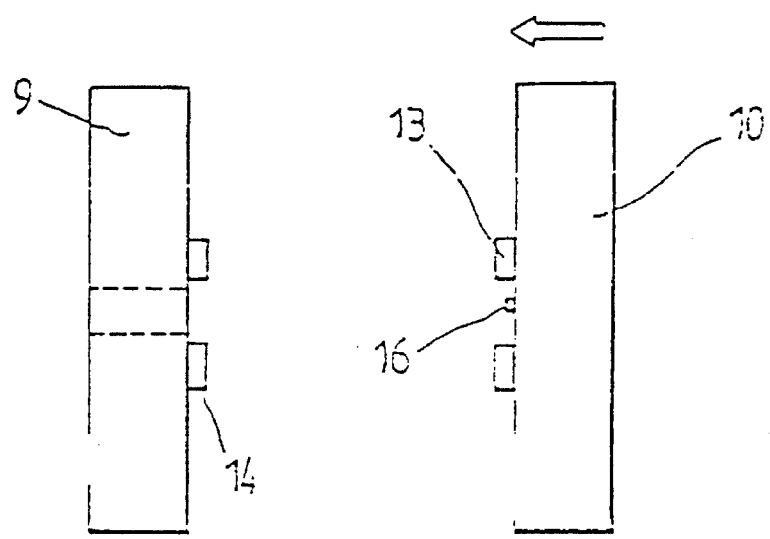
FIG. 5 shows the movable board moved back to its former position after the removal of the catheter.

The tipping process of the present invention is outlined hereinafter with reference to FIGS. 2 through 6. The steel needle 1 is inserted into one end (i.e., the rear end) of the catheter 2. Next, the catheter 2 is inserted through the hole 3, and the other end (namely, the front end) of the catheter 2 is then mounted on the circular pin 16. Next, the air pump 18 is operated to move the fixtures 13 and 14, thereby causing the fixture 14 on the first fixed board 9 to clamp the catheter 2 and the steel needle 1 and the fixture 13 on the movable board 10 to clamp the catheter 2 and the circular pin 16. Finally, the slide carriages 4 and 5 are moved to carry the nozzle 6 to the operative position around the catheter 2 (as shown in FIG. 2).

When the nozzle 6 has been moved to the operative position around the catheter 2, the heating device is turned on to send a current of hot air towards the catheter 2 through the nozzle 6 via the hot air pipe 7. The heating time is controlled by a timer (not shown). When the set length of time is up, the hydraulic device 19 is operated to move the movable board 10 towards the second fixed board 11 (see FIG. 3). The backward moving speed and distance are controlled by the control device. When the movable board 10 is moved backwards towards the second fixed board 11, the heated part 24 of the catheter 2 is pulled in reversed directions and becomes gradually reduced in diameter toward the center. Next, the piston rod 191 of the hydraulic device 19 is stopped (see FIG. 4), and the cooling device is then operated to send a current of cooling air to the catheter 2 through the nozzle 6 via the cold air pipe 8, thereby causing the catheter 2 to cool down. Following a predetermined length of time in cooling, the cooling device is shut off, then the slide carriages 4 and 5 are moved to carry the nozzle 6 away from the catheter 2. Next, the air pump 18 is operated to release the fixtures 13 and 14 from the catheter 2 permitting the catheter 2 with the steel needle 1 to be removed from the tipping device. The movable board 10 is moved towards the first fixed board 9 and stopped at its original position (see FIG. 5) for a next tipping operation. After the steel needle 1 is removed from the processed catheter 2, the front end of the catheter 2 is cut into a tapered tip 25 (see FIG. 7).

While only one embodiment of the present invention has been shown and described, it is assumed here that various modifications and changes could be made without departing from the spirit and scope of the invention. For example, the hydraulic device 19 for driving the movable board can be replaced by a pneumatic device and the air pump 18 for operating the pistons 13, 14 can be replaced by an hydraulic pump.

What is claimed is:

1. A tipping device for manufacturing medical catheters, the tipping device comprising:

a base;

a fixed front board vertically mounted on said base, said fixed front board comprising a mounting hole for receiving the catheter and a first clamping device disposed around said mounting hole;

a moveable board vertically movably mounted on said base and moved in parallel relative to said fixed front board, said movable board comprising a mounting pin longitudinally aligned with said mounting hole for holding a front end of the catheter and a second clamping device disposed around said mounting pin, the outer diameter of said mounting pin being smaller than the inner diameter of the catheter;

a first driving means controlled to reciprocate said movable board relative to said fixed front board;

a second driving means controlled to turn said first and second clamping devices each into an operative position to hold down the catheter and to release said first and second claiming devices from said operative position; and means for selectively heating and cooling down a part of the catheter between the first and second clamping devices.

2. The tipping device of claim 1 wherein said first and second driving means are hydraulic mechanisms.

3. The tipping device of claim 1 wherein said first and second driving means are pneumatic mechanisms.

4. The tipping device of claim 1 further comprising a fixed rear board vertically mounted on said base and oppositely paralleled to said fixed front board wherein said movable board is positioned in between and connected to said fixed front board and said fixed rear board by tie rods in four corners.

5. The tipping device of claim 4 wherein said tie rods support said movable board in parallel between said fixed front board and said fixed rear board, permitting said movable board to be reciprocated along said tie rods between said fixed front board and said fixed rear board.

6. The tipping device of claim 1 wherein said means for selectively heating and cooling down said part of the catheter provides hot or cold air through a nozzle.

* * * * *